United States Patent [19]

Seri et al.

[11] Patent Number: 5,468,734

[45] Date of Patent: Nov. 21, 1995

[54] PROPHYLACTIC AND REMEDIAL PREPARATION FOR DISEASES ATTENDANT ON HYPERGLYCEMIA, AND WHOLESOME FOOD

[75] Inventors: Kenji Seri, Yashio; Kazuko Sanai, Zama; Shigenori Negishi; Toshiro Akino, both of Soka, all of Japan

[73] Assignee: Godo Shusei Co., Ltd., Tokyo, Japan

[21] Appl. No.: 368,755

[22] Filed: Jan. 4, 1995

Related U.S. Application Data

[63] Continuation of Ser. No. 28,369, Mar. 8, 1993, abandoned.

[30] Foreign Application Priority Data

Mar. 10, 1992 [JP] Japan .................................. 4-086196
Dec. 21, 1992 [JP] Japan .................................. 4-355368

[51] Int. Cl.⁶ ...................... A61K 31/70; A61K 31/715; A23L 1/09
[52] U.S. Cl. ...................... 514/23; 514/824; 514/866; 514/909; 424/439
[58] Field of Search ................ 514/23, 866, 909, 514/824; 424/439

[56] References Cited

U.S. PATENT DOCUMENTS

| | | | |
|---|---|---|---|
| 4,708,950 | 11/1987 | Yoshikumi et al. | 536/22 |
| 4,745,185 | 5/1988 | Maryanoff et al. | 536/117 |
| 4,786,722 | 11/1988 | Zehner | 536/125 |
| 4,801,582 | 1/1989 | Hikino et al. | 514/866 |
| 5,064,659 | 11/1991 | Greenberg et al. | 426/271 |
| 5,064,672 | 11/1991 | Mazur | 426/531 |
| 5,124,360 | 6/1992 | Larner et al. | 514/866 |

FOREIGN PATENT DOCUMENTS

| 0456948 | 11/1991 | European Pat. Off. . |
|---|---|---|
| WO91/09604 | 7/1991 | WIPO . |

OTHER PUBLICATIONS

Sloviter et al., Proc. Int. Union Physiol. Sci., vol. 7, No. 24, 1968, p. 405.
Ishiwata et al., Endocrinol. Jpn., vol. 25, No. 2, 1978, pp. 163–169.
Ginsburg et al., Diabetes, vol. 19, No. 1, 1970, pp. 23–27.
Ginsburg et al., Acta Endocr. 9Suppl. 138), 1969, abstract No. 158.
Boll. Soc. Ital. Biol. Sper., vol. 41, No. 5, 1965, pp. 260–265.
Masao et al., Patent Abstracts of Japan, vol. 131, No. 51 (C-584), Apr. 12, 1989.
Semenza et al., *Eur. J. Biochem.*, 41, 149–162, 1974.

*Primary Examiner*—Ronald W. Griffin
*Attorney, Agent, or Firm*—Bacon & Thomas

[57] ABSTRACT

A prophylactic and remedial preparation for a disease attendant on hyperglycemia, a preparation for depressing the rise in blood sugar, and a wholesome food separately include, as an active ingredient, at least one component selected from the group consisting of L-arabinose, L-fucose, 2-deoxy-D-galactose, D-xylose, L-xylose, D-ribose, D-tagatose, D-ribulose, D-lyxose and D-xylulose.

5 Claims, No Drawings

PROPHYLACTIC AND REMEDIAL PREPARATION FOR DISEASES ATTENDANT ON HYPERGLYCEMIA, AND WHOLESOME FOOD

This application is a Continuation of application Ser. No. 08/028,369, filed Mar. 8, 1993, now abandoned.

BACKGROUND OF THE INVENTION i) Field of the Invention

This invention relates to drugs which are intended to prevent and remedy diseases attendant on hyperglycemia after each meal, for example, diabetes, prediabetes, obesity, hyperlipemia, arteriosclerosis, etc., and wholesome foods.

ii) Description of the Background Art

α-Glucosidases represented by sucrase and maltase are enzymes which bear a leading role in hydrolysis of carbohydrates in the intestine, and exert a vital influence on carbohydrate absorption. Therefore, sucrase inhibitors and maltase inhibitors are useful as preparations for depressing the rise in blood sugar after each meal (U.S. Pat. No. 4,062,950, Japanese Patent Application Laid-Open No. 156945/1989).

However, most of the conventionally-known sucrase inhibitors and maltase inhibitors were secondary metabolites produced by microorganisms and were not contained in foods generally ingested by human beings. Accordingly, these substances are foreign matters to the living body, and have hence been left a fear as to the safety in the case where they are taken up from the digestive tract into the blood and reach the systemic organs. In principal organs such as the liver, heart or skeletal muscle, in which the hydrolytic metabolism of carbohydrates actively takes place, in particular, a fear has been emphatically pointed out for long-term safety.

Accordingly, there has been a demand for development of an α-glucosidase inhibitor which is a substance contained in foods generally ingested, and is highly safe for the living body in that it is hard to be taken up from the digestive tract, is discharged quickly if taken up, and is hence not retained in the human body.

SUMMARY OF THE INVENTION

It is an object of this invention to provide a prophylactic and remedial preparation for the above-described symptoms and a wholesome food, which can solve the above-described problems involved in the prior art and comprises, as an active ingredient, an α-glucosidase inhibitor having excellent physical properties and physiological functions and derived from substances occurred in nature.

The present inventors have researched and studied the α-glucosidase-inhibiting actions, laying stress on the sucrase-inhibiting action and maltase-inhibiting action, of various pentoses, hexoses and oligosaccharides which occur in nature, and investigated in detail their actions to depress the rise in blood sugar after carbohydrate loading by using laboratory animals.

As a result, it has been found that some pentoses and hexoses including L-arabinose have strong sucrase-inhibiting action and maltase-inhibiting action, and moreover are remarkably effective in depressing the rise in blood sugar after carbohydrate loading, leading to completion of the present invention.

In an aspect of the present invention, there is thus provided a prophylactic and remedial preparation for a disease attendant on hyperglycemia, comprising, as an active ingredient, at least one component selected from the group consisting of L-arabinose, L-fucose, 2-deoxy-D-galactose, D-xylose, L-xylose, D-ribose, D-tagatose, D-ribulose, D-lyxose and D-xylulose.

In another aspect of this invention, there is also provided a prophylactic and remedial preparation composition for a disease attendant on hyperglycemia, comprising, as an active ingredient, at least one of the above-specified monosaccharides, and pharmaceutical additives.

In a further aspect of this invention, there is also provided a method of remedying a disease attendant on hyperglycemia, which comprises administering to a patient of the disease attendant on hyperglycemia at least one of the above-specified monosaccharides in an effective dose.

In still a further aspect of this invention, there is also provided a preparation composition for depressing the rise in blood sugar due to carbohydrate ingestion, comprising, as an active ingredient, at least one of the above-specified monosaccharides, and pharmaceutical additives.

In yet still a further aspect of this invention, there is also provided a method of depressing the rise in blood sugar due to carbohydrate ingestion, which comprises administering at least one of the above-specified monosaccharides in an effective dose.

In yet still a further aspect of this invention, there is also provided a wholesome food for preventing obesity, comprising at least one of the above-specified monosaccharides in a proportion of at least 2 wt. % of other carbohydrates than those specified herein.

According to the present invention, it has been confirmed that L-arabinose, L-fucose, 2-deoxy-D-galactose, D-xylose, L-xylose, D-ribose, D-tagatose, D-ribulose, D-lyxose and D-xylulose have an effective action to depress the rise in blood sugar for sucrose or starch loading.

The use of at least one of these compounds as an active ingredient makes it possible to provide, as a prophylactic and remedial preparation for diseases attendant on hyperglycemia, a prophylactic and remedial preparation free of any fear as to the safety for the living body, in particular, organs in which carbohydrate metabolism actively takes place, even when it is continuously used for a long period of time, and at the same time a wholesome food.

These and other objects and advantages of the present invention will become apparent from the preferred embodiments of this invention, which will be described subsequently in detail.

DETAILED DESCRIPTION OF THE INVENTION AND PREFERRED EMBODIMENTS

The monosaccharides useful in the practice of this invention are one or more compounds selected from the group consisting of L-arabinose, L-fucose, 2-deoxy-D-galactose, D-xylose, L-xylose, D-ribose, D-tagatose, D-ribulose, D-lyxose and D-xylulose. Among these compounds, L-arabinose is particularly preferred.

These monosaccharides strongly inhibit the hydrolysis of sucrose and maltose, which is catalyzed by α-glucosidases derived from the small intestine. They also have an action to depress the rise in blood sugar due to carbohydrate ingestion. These monosaccharides occur in nature and are substantially innoxious because they have not been reported to be poisonous to human beings and animals. In particular, L-arabinose is known to be hard to be taken up from the digestive tract and is considered to have no systemic influence.

No particular limitation is imposed on the additives incorporated into the prophylactic and remedial preparation composition for diseases attendant on hyperglycemia and the preparation composition for depressing the rise in blood sugar according to the present invention (hereinafter referred to as the "inventive compositions") so long as they are additives generally used in pharmaceutical preparations. As examples thereof, may be mentioned excipients, stabilizers, preservatives, binders, disintegrators and the like. Sucrose may be used as an edulcorant upon the formulation of these compositions. However, a low-caloric edulcorant such as aspartame or stevioside may be used. Examples of the form of the inventive compositions include a solution, capsule, granule, pill, powder and tablet. The inventive compositions or preparations may be administered either orally or enterally.

At least one of the above-specified monosaccharides or the inventive compositions may be suitably added to foods to provide wholesome foods for preventing and remedying diseases attendant on hyperglycemia, and preventing the rise in blood sugar due to carbohydrate ingestion and obesity. In the case where such a wholesome food is produced, the monosaccharide according to this invention may preferably be added in a proportion of 2.0 wt. % of other carbohydrates than those specified herein. Any proportions not lower than 2.0 wt. % permits sufficient depression of the rise in blood sugar due to carbohydrate ingestion. However, it is particularly preferred to add such a compound in a proportion of 2.0–50 wt. % of the other carbohydrates.

The dosing method and dose of the specified monosaccharide to a human being should be determined according to the age, weight and condition of the patient to be dosed. In many cases, however, the monosaccharide is preferably dosed in portions in a range of 0.5–3 g/day before each meal or during the meal.

EXAMPLES

The present invention will hereinafter be described in more detail by the following examples. However, it should be borne in mind that this invention is not limited to and by these examples only.

Example 1

(Action to inhibit the hydrolytic activity of homogenate prepared from rabbit small intestine mucous membrane to carbohydrate)

A native kind of white rabbits (weight: 3.0–3.5 kg) were sacrificed by exsanguination to take out their small intestines.

After freezing and thawing the small intestines thus taken out, they were homogenized in a 5 mM EDTA buffer (pH: 7.0) and subjected to centrifugation for 60 minutes at 60,000×g. Precipitate thus formed was collected and suspended again in a 10 mM potassium phosphate buffer (pH: 7.0), thereby obtaining a crude enzyme suspension.

Sucrose (20 mM) and maltose (20 mM) were used as substrates.

Each reaction mixture was formulated so as to contain 350 microliters of a 100 mM maleate buffer (pH: 6.8), 100 microliters of a substrate solution, 50 microliters of the crude enzyme suspension and 50 microliters of a test solution. Substances to be tested were separately dissolved in a maleate buffer (pH: 6.8) before use.

Respective reactions were conducted for 15 minutes at 37° C. The amounts of glucose formed were determined by the glucose oxidase method and are shown in Tables 1–3.

TABLE 1

Inhibiting action of monosaccharides (pentoses) on carbohydrases

| Substance tested | Concentration mg/dl | Inhibiting action on carbohydrase derived from rabbit small intestine mucous membrane (%) | |
|---|---|---|---|
| | | Sucrase inhibition rate | Maltase inhibition rate |
| D-Arabinose | 50 | 4.0 | |
| | 100 | 6.8 | |
| | 200 | 11.7 | 7.8 |
| L-Arabinose | 25 | 25.3 | 28.5 |
| | 50 | 37.8 | 35.8 |
| | 100 | 52.0 | 45.7 |
| | 200 | 66.3 | 47.4 |
| D-Xylose | 25 | 28.5 | 29.2 |
| | 50 | 35.5 | 36.4 |
| | 100 | 49.5 | 44.3 |
| | 200 | 59.8 | 53.1 |
| L-Xylose | 50 | 8.0 | |
| | 100 | 11.9 | |
| | 200 | 24.5 | 19.4 |
| D-Ribose | 25 | 13.7 | 13.5 |
| | 50 | 17.8 | 18.4 |
| | 100 | 34.0 | 33.3 |
| | 200 | 33.4 | 46.5 |
| D-Xylulose | 200 | 19.9 | 11.9 |
| L-Xylulose | 200 | 10.8 | 6.4 |
| D-Ribulose | 200 | 21.7 | 20.1 |
| D-Lyxose | 200 | 23.4 | 22.3 |
| L-Lyxose | 200 | −0.2 | 10.0 |

TABLE 2

Inhibiting action of monosaccharides (hexoses) on carbohydrases

| Substance tested | Concentration mg/dl | Inhibiting action on carbohydrase derived from rabbit small intestine mucous membrane (%) | |
|---|---|---|---|
| | | Sucrase inhibition rate | Maltase inhibition rate |
| 2-Deoxy-D-galactose | 25 | 13.7 | 11.2 |
| | 50 | 15.5 | 13.4 |
| | 100 | 21.6 | 19.3 |
| | 200 | 34.8 | 32.8 |
| D-Tagatose | 25 | 8.9 | 12.5 |
| | 50 | 15.7 | 17.7 |
| | 100 | 30.0 | 30.3 |
| | 200 | 36.6 | 33.9 |
| D-Fucose | 200 | 8.7 | 4.1 |
| L-Fucose | 25 | 11.6 | 16.4 |
| | 50 | 16.2 | 18.4 |
| | 100 | 32.8 | 24.8 |
| | 200 | 30.7 | 31.0 |

TABLE 2-continued

Inhibiting action of monosaccharides (hexoses) on carbohydrases

| Substance tested | Concentration mg/dl | Inhibiting action on carbohydrase derived from rabbit small intestine mucous membrane (%) | |
|---|---|---|---|
| | | Sucrase inhibition rate | Maltase inhibition rate |
| D-Talose | 200 | 5.4 | 5.3 |
| L-Sorbose | 200 | 5.1 | 7.5 |
| D-Mannose | 50 | −0.7 | 3.2 |
| | 100 | 12.9 | 10.6 |
| | 200 | 19.3 | 25.1 |
| | 400 | 27.8 | 30.4 |
| D-Galactose | 50 | −0.6 | −0.8 |
| | 100 | −0.9 | 13.9 |
| | 200 | 6.4 | 15.3 |
| | 400 | 20.2 | 11.8 |
| D-Galacto-samine | 200 | −6.5 | −4.5 |

TABLE 3

Inhibiting action of oligosaccharides on carbohydrases

| Substance tested | Concentration mg/dl | Inhibiting action on carbohydrase derived from rabbit small intestine mucous membrane (%) | |
|---|---|---|---|
| | | Sucrase inhibition rate | Maltase inhibition rate |
| Gentiobiose | 200 | −2.4 | 1.9 |
| Cellobiose | 200 | −0.4 | 2.8 |
| Xylooligo-saccharides β-1,4-(xylose)$_n$ | | | |
| n = 2 | 200 | 10.7 | 5.5 |
| n = 3 | 200 | 2.7 | 3.6 |
| n = 4 | 200 | 3.5 | 2.0 |
| n = 5 | 200 | −0.5 | 1.5 |
| n = 6 | 200 | −7.9 | −5.1 |
| Mannooligo-saccharides β-1,4-(mannose)$_n$ | | | |
| n = 2 | 200 | 0.9 | 0.6 |
| n = 3 | 200 | 2.0 | 1.3 |
| n = 4 | 200 | −0.3 | 0.7 |
| n = 5 | 200 | 4.0 | 3.5 |

As shown in Table 1, L-arabinose, D-xylose and D-ribose among the pentoses about which the inhibiting action had been investigated had strong sucrase-inhibiting action and maltase-inhibiting action, and L-xylose, D-xylulose, D-ribulose and D-lyxose exhibited inhibiting actions second to these.

However, no or little inhibiting action was recognized as to D-arabinose, L-lyxose and L-xylulose.

With respect to the hexoses, strong sucrase-inhibiting action and maltase-inhibiting action were recognized on 2-deoxy-D-galactose, D-tagatose and L-fucose. However, L-sorbose, D-fucose, D-talose, D-mannose, D-galactose and D-galactosamine showed no or little inhibiting action (Table 2).

With respect to the oligosaccharides, those having an effective inhibiting action on these enzymes were not found from the substances investigated (Table 3).

Example 2

(Action to depress the rise in blood sugar after carbohydrate loading)

ICR male mice (weight 30–35 g) were used in proportions of 5 mice per group.

After causing the mice to fast, sucrose or starch was orally administered in a proportion of 1 g/kg to the mice of each group, and at the same time substances to be tested were orally given to mice of their corresponding groups.

Blood was collected from the retroorbital sinus of each mouse before carbohydrate loading and upon elapsed times of 30 minutes, 60 minutes and 120 minutes after the loading to determine the concentration of glucose in the blood plasma by the glucose oxidase method.

As shown in Table 4, it was confirmed that the rise in blood sugar due to sucrose loading is depressed in dependence on the dose by L-arabinose and D-xylose (each orally administered in proportions of 25, 50 and 100 mg/kg), and moreover significantly depressed by D-tagatose, 2-deoxy-D-galactose, L-fucose, L-xylose, D-ribose, D-ribulose, D-lyxose, D-xylulose (each orally administered in a proportion of 100 mg/kg).

Further, L-arabinose exhibited a depressing action on the rise in blood sugar due to starch loading in dependence on the dose.

TABLE 4

Action to depress rise in blood sugar after carbohydrate loading to mice

| Carbohydrate loaded | Substance tested | Number of male mice tested | Dose mg/kg | Rise in blood sugar (Δmg/dl) | | |
|---|---|---|---|---|---|---|
| | | | | After 30 min. | After 60 min. | After 120 min. |
| Sucrose (1 g/kg) | Solvent (water) | 5 | Water | 94.2 ± 6.95 | 60.4 ± 7.10 | 28.3 ± 2.69 |
| | L-Arabinose | 5 | 25 | 71.7 ± 6.37* | 49.4 ± 5.73 | 25.4 ± 3.76 |
| | | 5 | 50 | 62.9 ± 6.19** | 37.3 ± 6.09* | 21.5 ± 3.90 |
| | | 5 | 100 | 41.8 ± 4.16*** | 30.4 ± 4.25** | 20.3 ± 3.76 |
| | D-Xylose | 5 | 25 | 76.3 ± 6.97 | 55.4 ± 4.75 | 27.3 ± 3.93 |
| | | 5 | 50 | 62.5 ± 6.38** | 47.3 ± 4.05 | 24.0 ± 2.60 |
| | | 5 | 100 | 38.2 ± 6.38*** | 45.2 ± 7.11 | 23.4 ± 4.42 |
| | D-Tagatose | 5 | 100 | 60.7 ± 7.28* | 44.4 ± 3.63 | 26.3 ± 3.38 |
| | 2-Deoxy-D- | 5 | 100 | 61.1 ± 7.21* | 50.8 ± 5.93 | 26.2 ± 3.10 |

TABLE 4-continued

Action to depress rise in blood sugar after carbohydrate loading to mice

| Carbohydrate loaded | Substance tested | Number of male mice tested | Dose mg/kg | Rise in blood sugar (Δmg/dl) | | |
|---|---|---|---|---|---|---|
| | | | | After 30 min. | After 60 min. | After 120 min. |
| | galactose | | | | | |
| | L-Fucose | 5 | 100 | 62.0 ± 6.63* | 44.4 ± 3.63 | 26.3 ± 3.38 |
| | L-Xylose | 5 | 100 | 66.3 ± 4.88* | 53.2 ± 4.91 | 27.3 ± 2.73 |
| | D-Ribose | 5 | 100 | 61.2 ± 7.91* | 48.5 ± 4.08 | 26.2 ± 3.06 |
| | D-Ribulose | 5 | 100 | 65.6 ± 5.04* | 56.3 ± 3.85 | 28.1 ± 3.43 |
| | D-Lyxose | 5 | 100 | 62.7 ± 6.73* | 57.0 ± 5.15 | 28.3 ± 3.19 |
| | D-Xylulose | 5 | 100 | 67.3 ± 4.32* | 59.7 ± 6.70 | 27.5 ± 3.90 |
| Starch | Solvent (water) | 5 | Water | 98.5 ± 6.58 | 71.9 ± 6.54 | 31.2 ± 2.52 |
| (1 g/kg) | L-Arabinose | 5 | 25 | 91.1 ± 6.87 | 68.5 ± 5.48 | 29.8 ± 2.41 |
| | | 5 | 50 | 71.4 ± 5.39* | 54.6 ± 5.74 | 26.6 ± 2.34 |
| | | 5 | 100 | 59.6 ± 4.51** | 48.3 ± 4.32* | 24.6 ± 1.96 |

Value of rise in blood sugar: Average value ± standard error;
*Level of significance p < 0.05 (to control);
**Level of significance p < 0.01 (to control);
***Level of significance p < 0.001 (to control).

Example 3

(Action to depress increase in body weight of mice)

ICR male mice after the elapse of 5 weeks from their birth were used in proportions of 10 mice per group.

After the mice were preliminarily bred for 1 week with a commercially-available ordinary feed ("Mouse-Rat Feed MF", product of Oriental Yeast Co., Ltd.), fully nutritious feeds to which L-arabinose had been added in proportions of 0.5% (Group 1), 1.0% (Group 2) and 2.0% (Group 3) (ordered products in the form of pellets, each making use, as a base, of a feed obtained by substituting 30% of the carbohydrate contained in an "Oriental Mixed Mouse-Rat Feed" produced by the same company as above with granulated sugar) were freely ingested to the mice of the respective groups.

Mice of a control group were caused to freely ingest the same feed as those used in the run groups except that L-arabinose was not added.

The mice of each group were separately weighed after 10 days, 20 days, 30 days and 60 days from the beginning of the ingestion to determine their weight increases from the initial weights, thereby calculating an average value of the weights increased in each group. The amounts of the feeds and water ingested were also determined.

During the experiment, the laboratory animals showed no abnormality in general medical condition and behavior, and had no death at all.

As shown in Table 5, the mice of the groups in which L-arabinose was added to their feeds showed less weight increases compared with the mice of the control group. This effect was dependent on the amount of L-arabinose added.

Any significant differences were not recognized as to the amounts of the feeds and water ingested.

TABLE 5

Action to depress increase in body weight of mice

| Run group | Concerns observed | After 10 days | After 20 days | After 30 days | After 60 days |
|---|---|---|---|---|---|
| A1 | Weight increase (g) | 5.9 | 9.2 | 12.4 | 15.0 |
| | Amount of feed ingested (g/day) | 2.9 | 3.1 | 3.4 | 3.9 |
| | Amount of water ingested (g/day) | 2.1 | 2.7 | 2.8 | 3.1 |
| A2 | Weight increase (g) | 5.3 | 8.0 | 11.7 | 13.8 |
| | Amount of feed ingested (g/day) | 2.8 | 3.1 | 3.4 | 3.8 |
| | Amount of water ingested (g/day) | 2.3 | 2.8 | 3.0 | 3.2 |
| A3 | Weight increase (g) | 4.7 | 7.2 | 10.2 | 12.1 |
| | Amount of feed ingested (g/day) | 2.7 | 3.1 | 3.3 | 3.7 |
| | Amount of water ingested (g/day) | 2.3 | 2.9 | 3.1 | 3.3 |
| Control | Weight increase (g) | 6.2 | 10.3 | 14.5 | 18.1 |
| | Amount of feed ingested (g/day) | 2.8 | 3.1 | 3.6 | 3.9 |
| | Amount of water ingested (g/day) | 2.1 | 2.7 | 2.9 | 3.2 |

What is claimed is:

1. A method of remedying a disease attendant on hyperglycemia, which comprises administering to a patient of the disease attendant on hyperglycemia an effective amount of at least one monosaccharide selected from the group consisting of L-arabinose, L-fucose, 2-deoxy-D-galactose, D-xylose, L-xylose, D-ribose, D-ribulose, D-lyxose and D-xylulose.

2. The method as claimed in claim 1, wherein the disease attendant on hyperglycemia is diabetes, prediabetes, obesity, hyperlipemia or arteriosclerosis.

3. A method according to claim 1 wherein the monosaccharide is L-arabinose.

4. A method of depressing the rise in blood sugar due to carbohydrate ingestion, which comprises administering an effective amount of at least one monosaccharide selected from the group consisting of L-arabinose, L-fucose, 2-deoxy-D-galactose, D-xylose, L-xylose, D-ribose, D-ribulose, D-lyxose and D-xylulose.

5. A method according to claim 4 wherein the monosaccharide is L-arabinose.

* * * * *